United States Patent
Clevenger et al.

(10) Patent No.: US 6,768,063 B2
(45) Date of Patent: Jul. 27, 2004

(54) STRUCTURE AND METHOD FOR SHADOW MASK ELECTRODE

(75) Inventors: Lawrence A. Clevenger, LaGrangeville, NY (US); Louis L. Hsu, Fishkill, NY (US); Carl J. Radens, LaGrangeville, NY (US); Li-Kong Wang, Montvale, NJ (US); Kwong Hon Wong, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 99 days.

(21) Appl. No.: 09/943,827

(22) Filed: Aug. 31, 2001

(65) Prior Publication Data

US 2003/0042043 A1 Mar. 6, 2003

(51) Int. Cl.⁷ .......................... H05K 1/11; H01R 12/04
(52) U.S. Cl. ........................ 174/267; 174/250; 257/737; 257/750; 438/666
(58) Field of Search ................................ 174/250, 267; 257/734, 750, 773, 737; 438/618, 666

(56) References Cited

U.S. PATENT DOCUMENTS

| | | | |
|---|---|---|---|
| 4,075,416 A | * | 2/1978 | Kuttner et al. ............... 174/257 |
| 4,626,479 A | * | 12/1986 | Hosoi et al. ................ 428/663 |
| 5,252,292 A | * | 10/1993 | Hirata et al. ................... 422/98 |
| 5,457,396 A | * | 10/1995 | Mori et al. ................. 324/724 |
| 5,473,197 A | * | 12/1995 | Idaka et al. ................ 257/786 |
| 6,108,212 A | | 8/2000 | Lach et al. |
| 6,111,204 A | * | 8/2000 | Goenka ....................... 174/257 |
| 6,306,559 B1 | * | 10/2001 | Tanamura et al. .......... 430/315 |
| 6,342,730 B1 | * | 1/2002 | Jung et al. .................. 257/692 |
| 6,492,197 B1 | * | 12/2002 | Rinne .......................... 438/108 |

FOREIGN PATENT DOCUMENTS

| | | | |
|---|---|---|---|
| JP | 402273926 A | 11/1990 | |
| JP | 407058439 A | 3/1995 | |

* cited by examiner

Primary Examiner—Kamand Cuneo
Assistant Examiner—I B Patel
(74) Attorney, Agent, or Firm—McGinn & Gibb, PLLC; Louis Percello, Esq.

(57) ABSTRACT

A method and structure for an electrode device, whereby a second electrode is deposited on a first electrode such that there is an increase in the capacitive coupling between the pair of conductive electrodes. The electrodes are self-aligning such that the patterning manufacturing process is insensitive to variations in the positional placement of the pattern on the substrate. Moreover, a single lithographic masking layer is used for forming the pair of electrodes, which are electrically isolated. Finally, the first electrode is offset from the second electrode by a chemical surface modification of the first electrode, and an anisotropic deposition of the second electrode which is shadowed by the first electrode.

14 Claims, 4 Drawing Sheets

STRUCTURE AND METHOD FOR SHADOW MASK ELECTRODE

BACKGROUND OF THE INVENTION

1. Field of the Invention

The present invention generally relates to an interdigitated electrode structure, and more particularly to a new structure for a pair of electrodes using conductive polymers, and a method for producing the same.

2. Description of the Related Art

An interdigitated electrode structure is used in applications where it is desirable to form a large perimeter surface area for interaction between the electrodes. Applications using this type of structure may include capacitors, sensors, and detectors. In a conventional interdigitated structure, the proximity of the electrodes is limited by a minimum lithographic feature, and hence the capacitance, or electric field intensity between the electrodes is constrained by the lithographic process.

Electronically conducting polymers, particularly derivatives of polypyrrole and polyaniline, in which the conducting form of the polymers is soluble in appropriate organic solvents, have been used in many electronic applications. These polymers can be applied onto silicon wafers by spin-on or silk screening techniques. For example, conducting polypyrrole has been proposed as an ingredient to make passive elements such as resistors, capacitors and inductors in multichip modules or printed wiring boards, as disclosed in U.S. Pat. No. 5,855,755, the complete disclosure of which is incorporated by reference herein.

Moreover, polypyrrole and polythiophene derivatives have been used in solid state electrochromic devices. The polypyrrole conducting polymer can be made to be photosensitive by adding appropriate silver salts and photoinitator additives, as disclosed in U.S. Pat. No. 5,919,402, the complete disclosure of which is incorporated by reference herein. It has been discovered that under optimized conditions, the conductivity value for poly (3-methylthiophene) is 5.7 $\Omega^{-1}$ cm$^{-1}$. Electrical conductivity can be further increased by incorporating metal particles such as nanoparticles of silver or copper in the polymer formulation. Thus, there is a need for an improved interdigitated electrode structure, which is capable of providing higher capacitance or electric field intensity between electrodes on electrical components of printed circuit boards and multichip modules, etc.

SUMMARY OF THE INVENTION

In view of the foregoing and other problems, disadvantages, and drawbacks of the conventional interdigitated electrode structure the present invention has been devised, and it is an object of the present invention to provide a structure and method for an improved interdigitated electrode structure. It is a further object of the present invention to increase the capacitive coupling between a pair of conductive electrodes on a substrate. The capacitive coupling will be a function of the distance between the pair of electrodes, and will increase as the electrodes are brought into close proximity.

Another object of the present invention is to provide a structure for a pair of electrodes which are self-aligned to each other. The self-aligned formation of the pair of electrodes means that the patterning manufacturing process will be insensitive to variations in the positional placement of the pattern on the substrate. Still another object of the present invention is to provide a method for forming the pair of electrodes using a single lithographic masking layer where the material modification of one of the electrodes causes an overhanging region to be formed on a first electrode which is used in the formation of the second electrode.

Yet another object of the present invention is to provide a structure which consists of a pair of electrodes which are electrically isolated, yet closer in proximity than the minimum resolvable lithographic feature size of the imaging system used to pattern the electrodes. The proximity of the electrodes is determined by the chemical surface modification, and the physical deposition of the second electrode, and not by the lithographic resolution as is the case in a conventional structure.

It is still another object of the present invention to provide a structure and method for the use of a conductive polymer for one or both electrode elements in a structure where the offset between the pair of electrodes is provided by a chemical surface modification ("swelling") of the first electrode, and an anisotropic deposition of the second electrode which is shadowed by the first electrode.

In order to attain the objects suggested above, there is provided, according to one aspect of the invention a method of producing an electrode device, which comprises the steps of first depositing a conductive polymer material on a substrate. Then, patterning a mask on top of the conductive polymer. Third, forming spaced regions on top of the substrate. Next, the mask is removed from the conductive polymer. After which, the conductive polymer is expanded such that an upper part of the conductive polymer upwardly slopes from the lower part of the conductive polymer material. Then, a second conductive material is deposited on top of the first conductive polymer material, and in the spaced regions, which are located on the substrate. Finally, several electrical connections are placed on the device.

The benefits of this invention are several. For example, the present invention provides for a self-aligned pair of electrodes, which can be easily fabricated. Furthermore, the present invention provides for a single lithographic masking level, and for sub-lithographic features. Additionally, the structure of the present invention provides for the sub-lithographic proximity of the upper and lower electrodes.

BRIEF DESCRIPTION OF THE DRAWINGS

The foregoing and other objects, aspects and advantages will be better understood from the following detailed description of a preferred embodiment(s) of the invention with reference to the drawings, in which.

DETAILED DESCRIPTION OF PREFERRED EMBODIMENTS OF THE INVENTION

As mentioned above, there is a need for new interdigitated electrode structures capable of providing increased capacitive coupling between a pair of electrically isolated electrodes on the substrate, where the electrodes are self-aligned to each other, are formed using a single lithographic masking layer, and are made with a conductive polymer material.

In a preferred embodiment of the present invention, the shadow mask first electrode is formed using a conductive polymer thin film material which is patterned and subjected to a surface modification to create an overhang such as that used in a conventional "liftoff" process. Surface modifications may include subjecting the first electrode (conductive polymer) to a wet chemical solvent which causes a volume expansion in the outer layer of the polymer, and hence a "swelling" along the surface of the polymer. This effect is applied to a photoresist, which is used in the well known microelectronic liftoff process. The complementary second electrode is formed by anisotropic deposition of a conductor such as physical vapor deposition (PVD) or sputtering, or evaporation from a point source.

Figure 1:
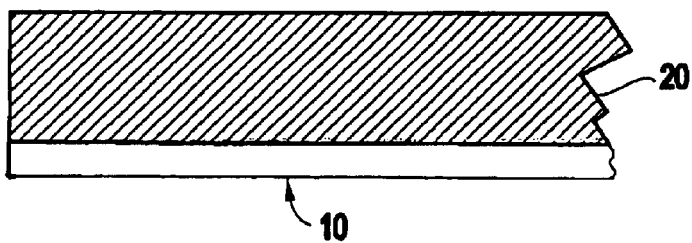
FIG. 1 is a schematic diagram of a partially completed interdigitated electrode structure according to the present invention.

An example of fabricating such an improved structure is shown in FIGS. 1–9. However, as would be known to one ordinarily skilled in the art given this disclosure, the invention is not limited to the example shown and is applicable to all similar structures. Referring now to the drawings, and more particularly to FIG. 1, there are shown preferred embodiments of the method and structures according to the present invention.

Figure 2:
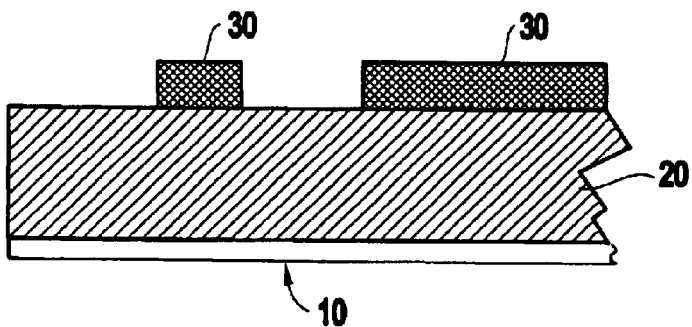
FIG. 2 is a schematic diagram of a partially completed interdigitated electrode structure according to the present invention.

FIG. 1 shows a conductive polymer thin film material 20 disposed on a substrate 10. FIG. 2 shows a mask 30 patterned on the conductive polymer 20 using conventional lithography and etching or by the addition of photoactive materials to the conductive polymer 20 and lithography. The conventional lithographic patterning comprises coating of a photoactive organic polymer over the conductive polymer 20. Then, exposure and development of selected regions to create a pattern of masking photoresist is performed. A dry or wet etch is then used to pattern the conductive polymer 20. Thereupon, the masking film is removed by dry or wet processing.

Alternatively, the conductive polymer film 20 may include photoactive compounds and be directly patterned by lithography. A conductive polymer such as polyphenylenevinylene, polypyrrole, polythiophene derivatives or any other electrically conductive polymer can be used. Finally, a proper low-temperature annealing can be applied to the polymer film.

Figure 3:
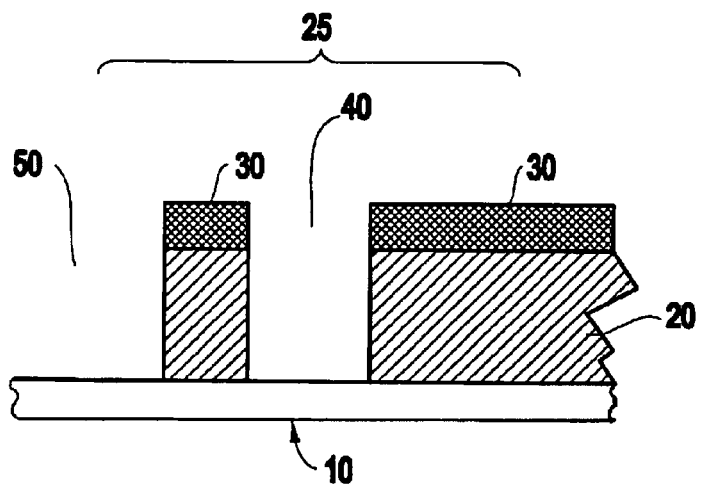
FIG. 3 is a schematic diagram of a partially completed interdigitated electrode structure according to the present invention.
Figure 4:
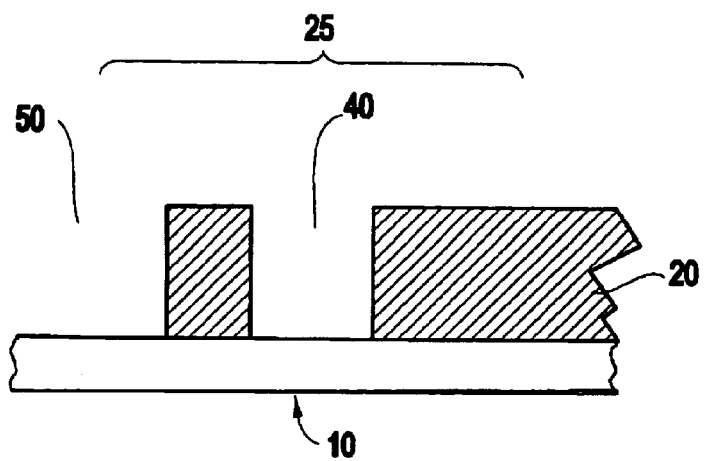
FIG. 4 is a schematic diagram of a partially completed interdigitated electrode structure according to the present invention.

Next, FIG. 3 illustrates the patterned conductive polymer 20 with narrow space region 40 and wide space region 50, which form the first electrode 25. FIG. 4 shows the patterned conductive polymer 20 with the masking material removed. Again, the masking film is removed by dry or wet processing.

Patterning of the conducting polymer 20 can be done by conventional photoresist technology where a layer of photoresist of given thickness is spin coated, exposed and developed first, then the pattern is transferred to the underlying conducting polymer by reactive ion etching (RIE) the unprotected polymer. Alternatively, laser photoablation can be used to pattern the conducting polymer. In yet another integration scheme, a photosensitive conducting polymer can be used. And finally, photopatterning by electrochemical polymerization and direct nanoimprint can also be used.

Figure 5:
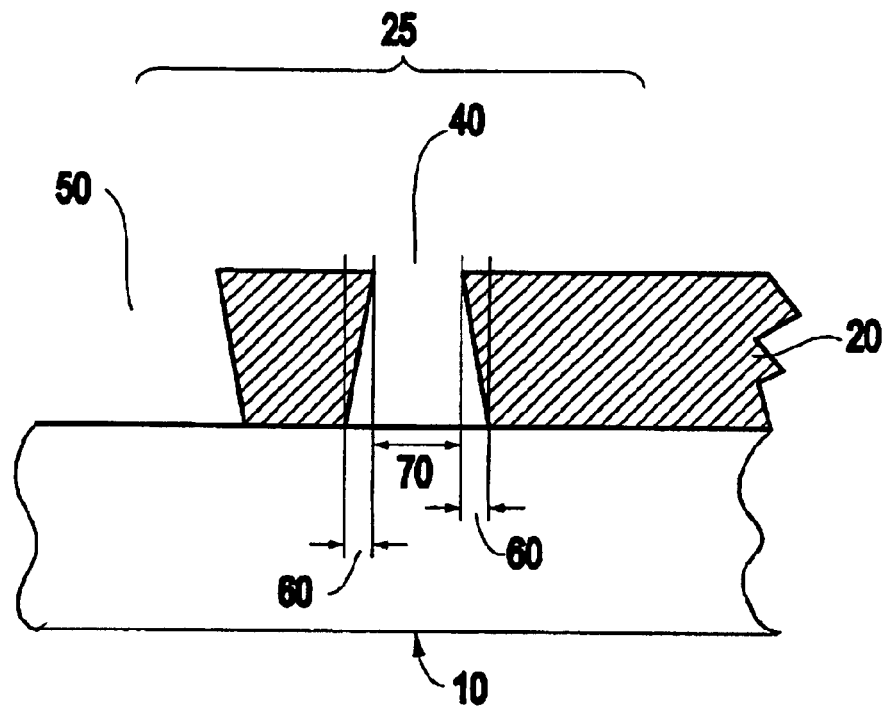
FIG. 5 is a schematic diagram of a partially completed interdigitated electrode structure according to the present invention.

In FIG. 5, the conductive polymer 20 is subjected to a surface volume expansion (swelling) to create overhang regions 60 and a narrowing of narrow space region 40 to a new space 70. The phenomenon of polymer swelling upon exposure to appropriate gases or organic solvents is well known to those skilled in the art. The degree of swelling is a function of the chemical nature of variables such as the gas/solvent used, the temperature and exposure time.

Figure 6:
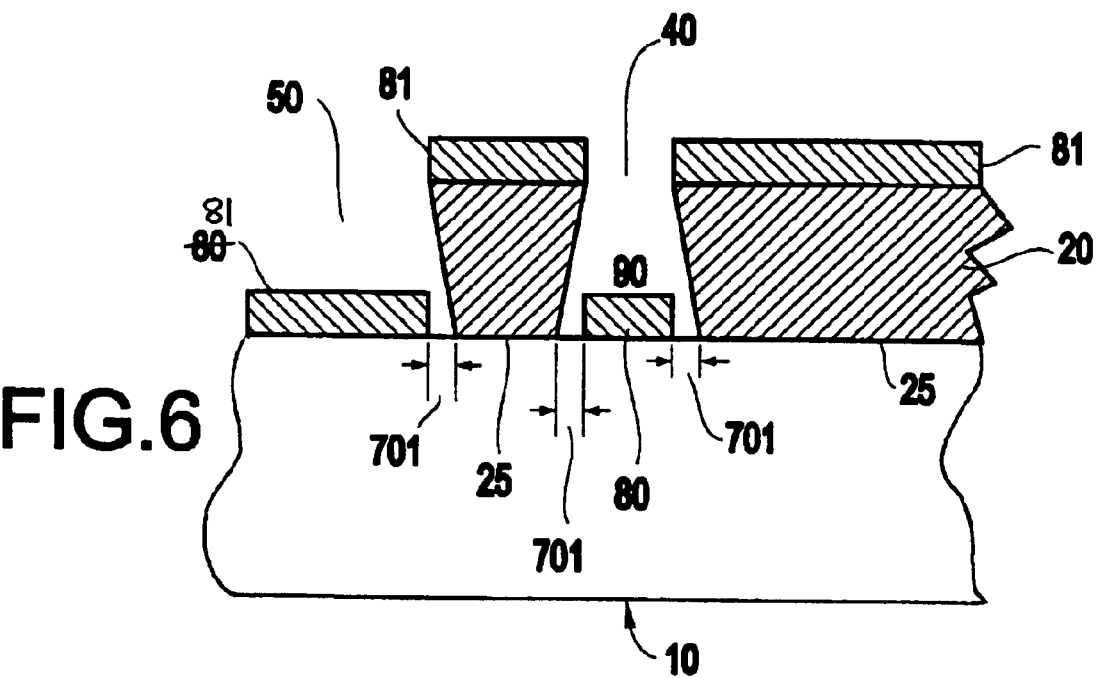
FIG. 6 is a schematic diagram of a partially completed interdigitated electrode structure according to the present invention.

In one example, one can subject the wafer substrate, in an enclosed chamber, with a shower head facing the polymer. The chamber is first equilibrated with an inert gas such as argon or helium. Then, a stream of reactive gas is directed towards the polymer surface through the shower head for a predetermined time. An alternative approach is to have the polymer film in contact with a soft pad pre-soaked with the swelling organic solvent. When the desirable overhang is reached, the silicon wafer is removed and electrodes can be deposited as shown in FIG. 6. Yet another approach is to incorporate a co-polymer into the conducting polymer blend. The chosen co-polymer will undergo an irreversible swelling due to de-polymerization upon exposure to an appropriate chemical while leaving the conducting polymer network unchanged. This last approach offers a wider choice of material that can be surface modified.

FIG. 6 also shows the anisotropic deposition of a second electrode 81 on the upper regions of the first electrode 25. Moreover the second electrode material 81 is also deposited in the complementary regions 90 and gap 50 to form the overall second electrode 81. The second electrode material 81 is comprised from a conductive material such as aluminum, copper, titanium, titanium nitride, sputtered tungsten, and is deposited by evaporating, sputtering or physical vapor deposition.

FIG. 6 best illustrates the purpose of the novel aspects of this invention, namely incorporating the surface volume expansion to electrode manufacturing. The purpose of the surface volume expansion is to ensure that there is proper spacing between the first electrode 25 and the second electrode 81. Thereby, ensuring that the electrodes are electrically isolated. Because the second electrode 81 is deposited by anisotropic deposition, the second electrode 81 only adheres to the exposed horizontal surface of the substrate. Thus, when the upper regions of the first electrode 25 swell, it prevents the second electrode 81 from being deposited in the space 701, which again, ensures that the electrodes are electrically isolated. Therefore, the electrodes are self-aligned because only one lithographic mask 30 (shown in FIG. 2) is used to pattern both the first and second electrode.

Figure 7:
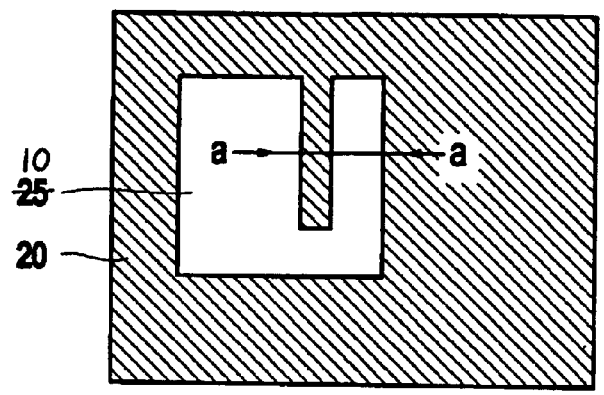
FIG. 7 is a schematic diagram of a partially completed interdigitated electrode structure according to the present invention.
Figure 8:
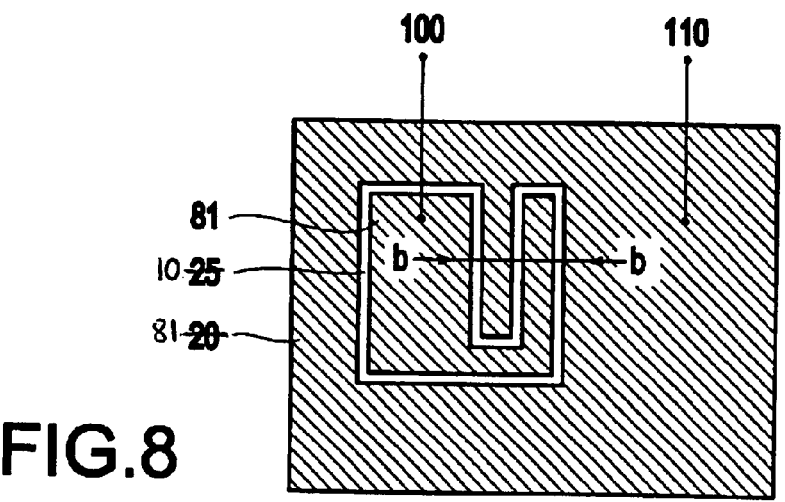
FIG. 8 is a schematic diagram of a partially completed interdigitated electrode structure according to the present invention.
Figure 9:
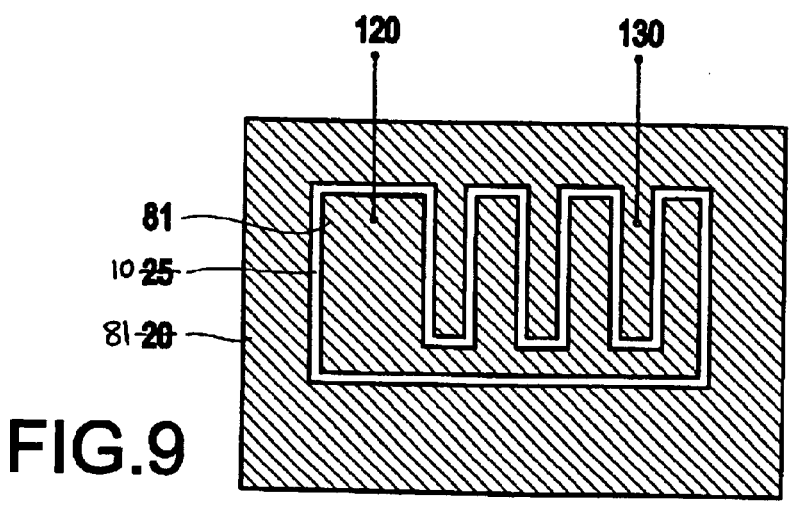
FIG. 9 is a schematic diagram of a partially completed interdigitated electrode structure according to the present invention.

FIG. 7 shows a top-down view of a pattern for the first electrode 25, with the cross section view a—a indicated for FIG. 5. FIG. 8 shows the top-down view after the deposition of the second electrode 81 with electrical connection 100 and 110 indicated. The cross sectional area defined by the line b—b is shown in the cross sectional view of FIG. 6. FIG. 9 shows a top-down view with a plurality of electrode fingers provided to enlarge the perimeter between the two electrodes, and hence enhance electrical interaction between the two electrodes. Electrical connections 120 and 130 are indicated as well.

Figure 10:
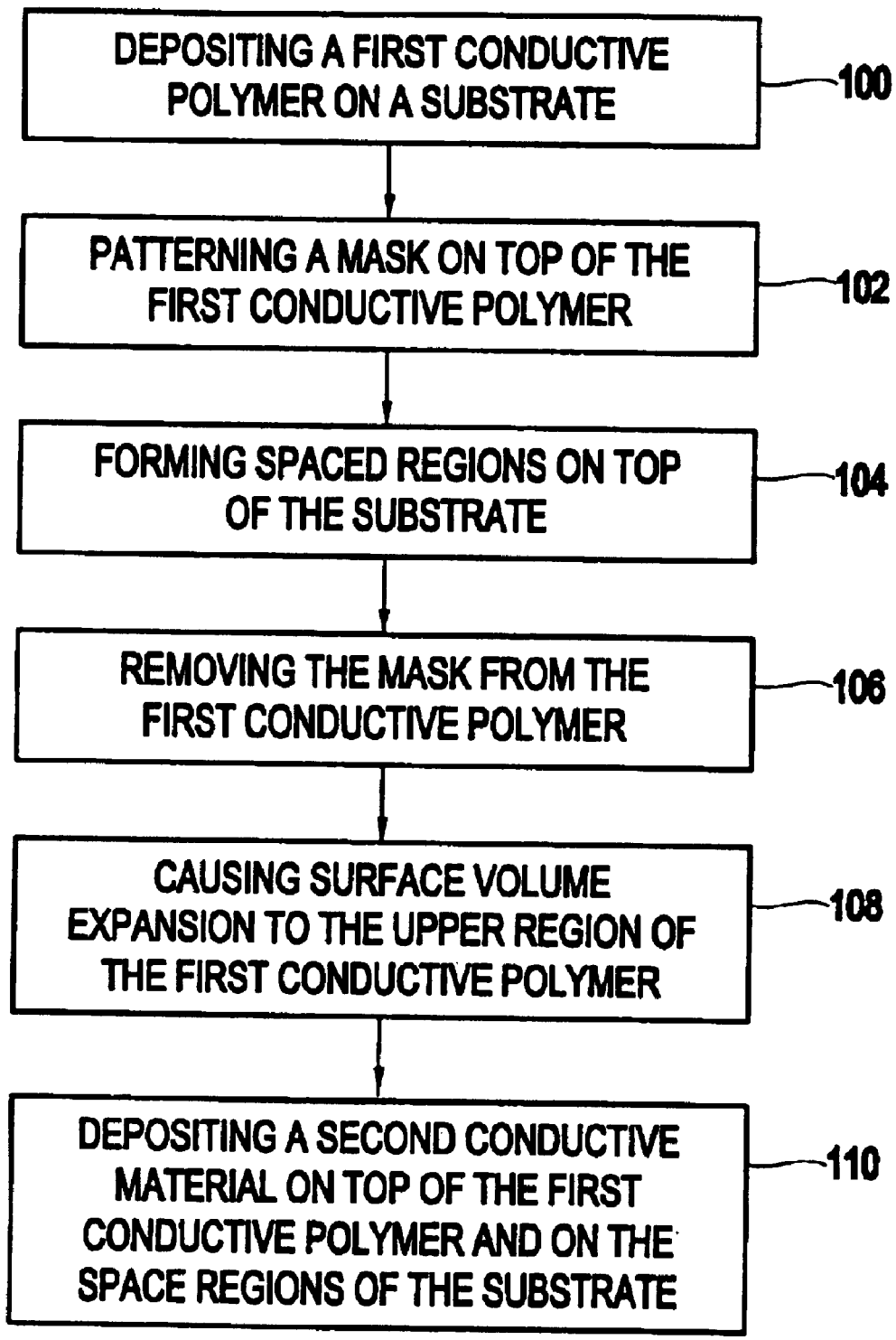
FIG. 10 is a flow diagram illustrating a preferred method of the invention.
Figure 1:
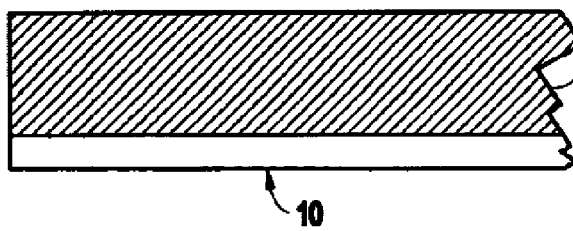
Figure 2:
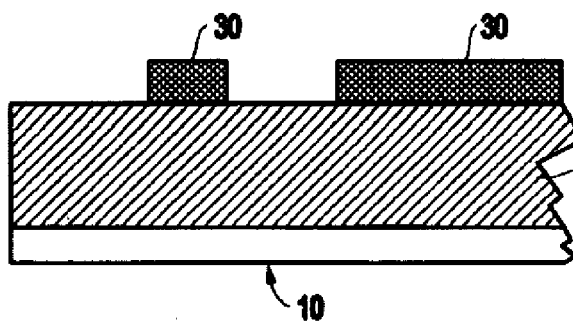
Figure 3:
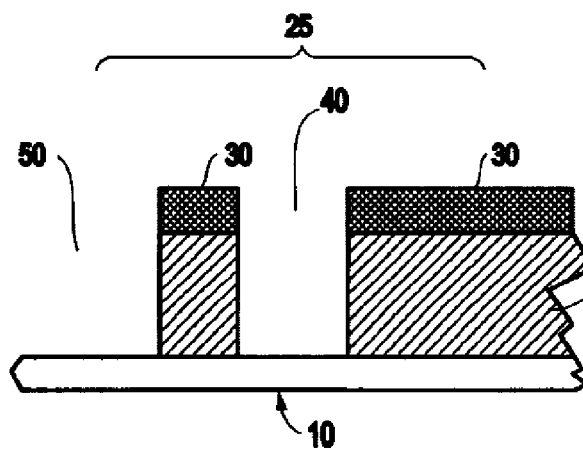
Figure 4:
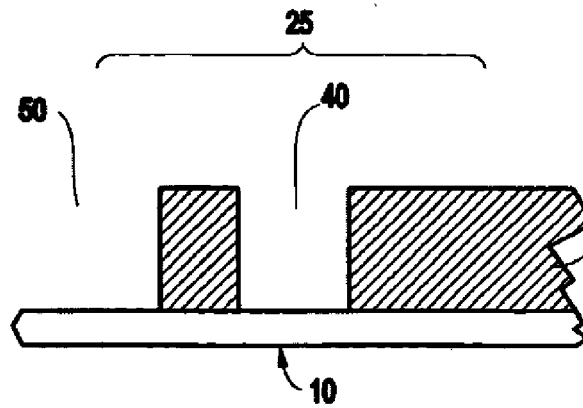
Figure 5:
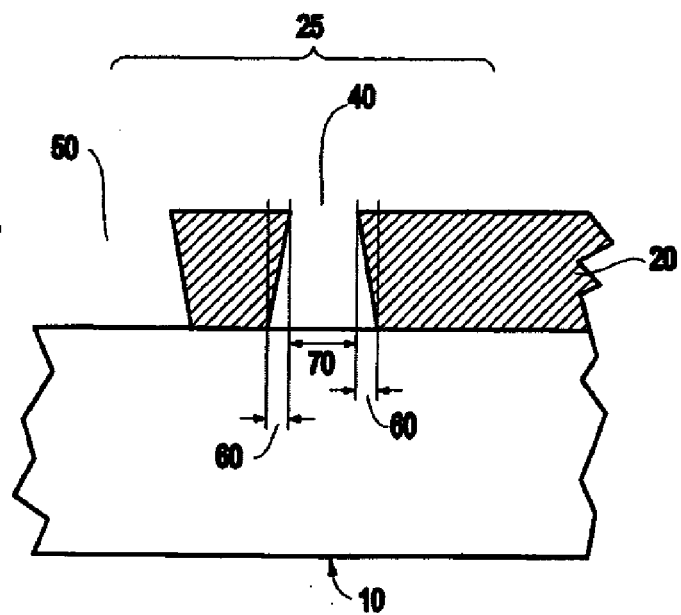
Figure 6:
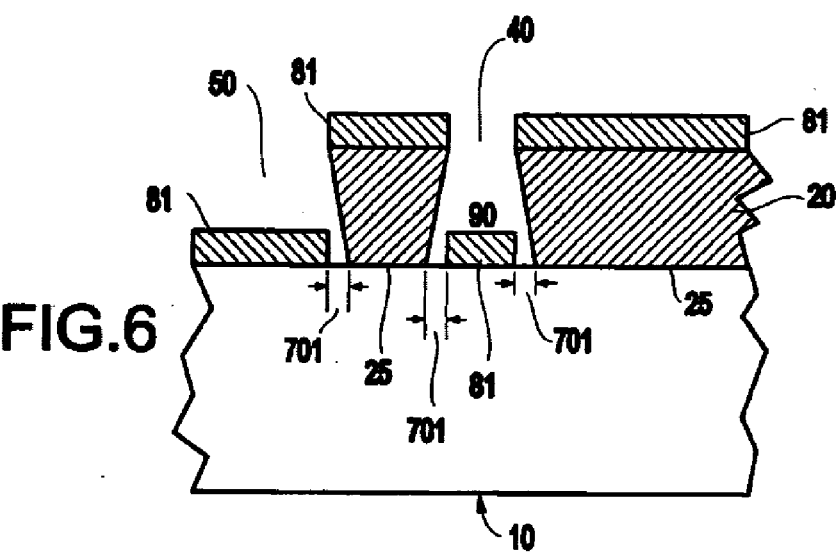
Figure 7:
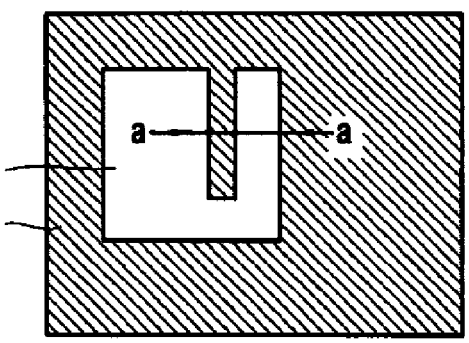
Figure 8:
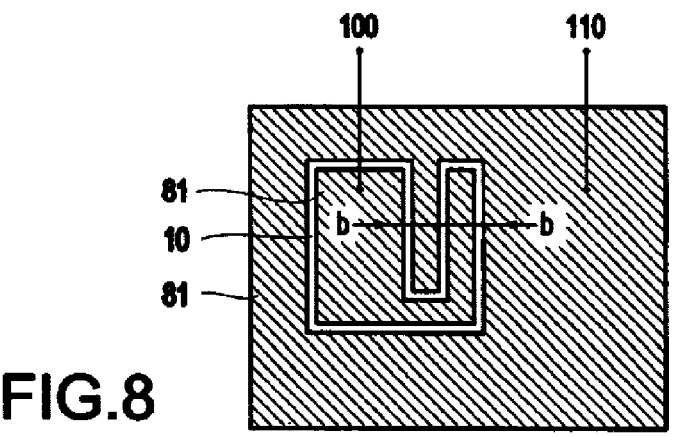
Figure 9:
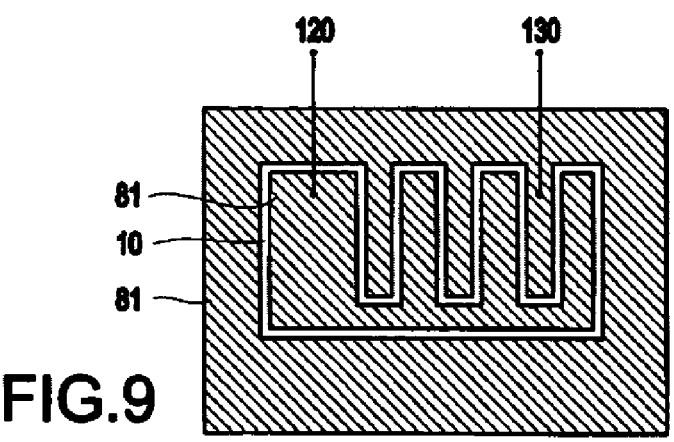
Figure 10:
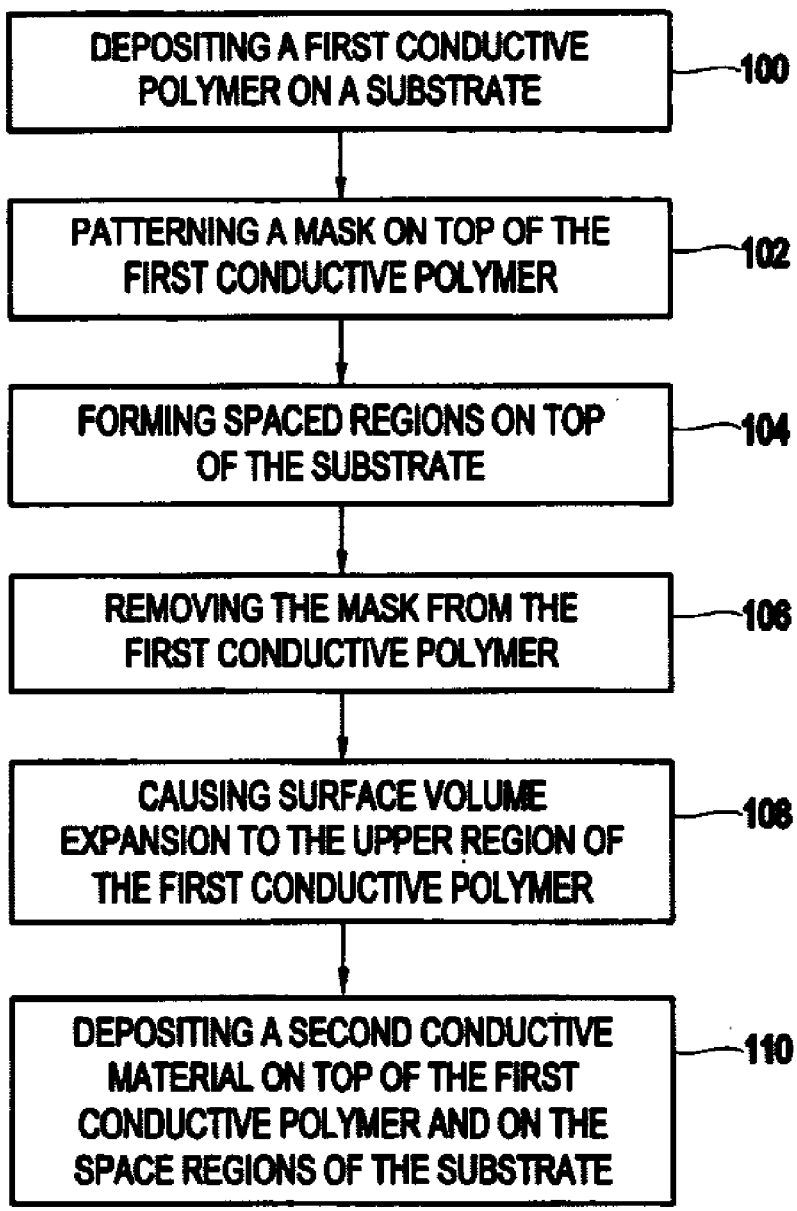

FIG. 10 illustrates the flow diagram of the entire process. Step 100 indicates that a first conductive polymer material is deposited on a substrate. Then in step 102, a mask is patterned on top of the first conductive polymer. Next, step 104 shows that spaced regions are formed on top of the substrate. Step 106 follows by removing the mask from the first conductive polymer. The next step is step 108, in which the upper region of the first conductive polymer undergoes surface volume expansion. Finally, in step 110, a second conductive material is deposited on top of the first conductive polymer and on the spaced regions on the substrate.

It is apparent that the pattern of the second electrode will be the complement of the pattern of the first electrode, and that the second electrode will be self-aligned with respect to the first electrode. In addition, the spacing between the two electrodes will be determined by the chemical surface modification of the first electrode, and not by a photolithographic patterning, and hence the proximity of the two electrodes will not be constrained by the lithographic process capability.

As previously mentioned, the benefits of this invention are several. For example, the present invention provides for a self-aligned pair of electrodes, which can be easily fabricated. Furthermore, the present invention provides for a single lithographic masking level, and for sub-lithographic features. Additionally, the structure of the present invention provides for the sub-lithographic proximity of the upper and lower electrodes.

While the invention has been described in terms of preferred embodiments, those skilled in the art will recognize that the invention can be practiced with modification within the spirit and scope of the appended claims.

What is claimed is:

1. An electrode device comprising electrodes with a plurality of electrode fingers, finger comprises said device comprising:
   a substrate;
   a first electrode formed of a first electrode material adjacent to said substrate, wherein said first electrode comprising an upper region and a lower region, wherein said device upper region is wider than said lower region; and
   a second electrode formed of a second electrode material in a region between each of said electrode fingers, wherein a same electrode material as said second electrode material is disposed on top of said first electrode.

2. The device of claim 1, wherein said electrode device further comprises a plurality of electrical connections.

3. The device of claim 1, wherein said upper region upwardly slopes from said lower region.

4. The device of claim 1, wherein said first electrode comprises a first electrically conductive material, and said second electrode comprises a second electrically conductive material.

5. The device of claim 4, wherein said first and first conductive material further comprises photoactive compounds, wherein said photoactive compounds comprises one of polyphenylenevinylene, polypyrrole, and polythiophene derivatives.

6. The device of claim 4, wherein said second conductive material comprises one of aluminum, copper, titanium nitride, sputtered tungsten, tantulum, and tantulum nitride.

7. An electrode device comprising electrodes with a plurality of electrode fingers, said device comprising:
   a substrate:
   a first electrode adjacent to said substrate, wherein said first electrode comprises an upper region and a lower region, wherein said upper region is wider than said lower region;
   a second electrode in a region in between each of said electrode fingers; and
   a plurality of electrical connections;
   wherein said upper region upwardly slopes from said lower region;
   wherein said first electrode comprises a first conductive material, and said second electrode comprises a second conductive material;
   wherein said first and second conductive material are electrically conductive; and
   wherein a same electrode material as said second conductive material is disposed on top of said first electrode.

8. The device of claim 7, wherein said first conductive material further comprises photoactive compounds, wherein said photoactive compounds comprise one of polyphenylenevinylene, polypyrrole, and polythiophene derivatives.

9. The device of claim 7, wherein said second conductive material comprises one of aluminum, copper, titanium, titanium nitride, sputtered tungsten, tantulum, and tantulum nitride.

10. An electrode device comprising electrodes with fingers, said device comprising:
    a substrate;
    a first electrode formed of a first electrode material adjacent to said substrate and configured to have an upwardly sloping configuration;
    a second electrode formed of a second electrode material adjacent to said first electrode and disposed in a region adjacent to a lower portion of said first electrode, wherein a same electrode material as said second electrode material is disposed on top of said first electrode; and
    a gap separating said lower portion of said first electrode from said second electrode in said region.

11. The device of claim 10, wherein said electrode device further comprises a plurality of electrical connections.

12. The device of claim 10, wherein said first electrode comprises a first electrically conductive material, and said second electrode comprises a second electrically conductive material.

13. The device of claim 12, wherein said first conductive material further comprises photoactive compounds, wherein said photoactive compounds comprise one of polyphenylenevinylene, polypyrrole, and derivatives.

14. The device of claim 12, wherein said second conductive material comprises one of aluminum, copper, titanium nitride, sputtered tungsten, tantulum, and tantulum nitride.

* * * * *

UNITED STATES PATENT AND TRADEMARK OFFICE
CERTIFICATE OF CORRECTION

PATENT NO. : 6,768,063 B2
DATED : July 27, 2004
INVENTOR(S) : Clevenger et al.

It is certified that error appears in the above-identified patent and that said Letters Patent is hereby corrected as shown below:

Drawings,
Please replace Figures 1-10 with the attached Formal Drawings

Column 5,
Line 44, "comprising" should be -- comprises --
Line 45, "wherein said device upper region" should be -- wherein said upper region --
Lines 60-61, "said first and first conductive" should be -- said first conductive --
Lines 62-63, "comprises" should be -- comprise --

Column 6,
Lines 2-3 and 58-59, "copper, titanium nitride, sputtered tungsten," should be -- copper, titanium, titanium nitride, sputtered tungsten, --

Signed and Sealed this

Fourteenth Day of June, 2005

JON W. DUDAS
*Director of the United States Patent and Trademark Office*